US012246034B2

(12) United States Patent
Van Den Bosch et al.

(10) Patent No.: US 12,246,034 B2
(45) Date of Patent: *Mar. 11, 2025

(54) ANIMAL FEED SUPPLEMENT AND METHOD

(71) Applicant: CAN TECHNOLOGIES, INC., Wayzata, MN (US)

(72) Inventors: Moniek Van Den Bosch, Boxmeer (NL); Ad Van Wesel, Made (NL)

(73) Assignee: CAN TECHNOLOGIES, INC., Wayzata, MN (US)

( * ) Notice: Subject to any disclaimer, the term of this patent is extended or adjusted under 35 U.S.C. 154(b) by 238 days.

This patent is subject to a terminal disclaimer.

(21) Appl. No.: 17/213,013

(22) Filed: Mar. 25, 2021

(65) Prior Publication Data
US 2021/0283175 A1 Sep. 16, 2021

Related U.S. Application Data

(62) Division of application No. 15/533,120, filed as application No. PCT/US2015/064293 on Dec. 7, 2015, now Pat. No. 10,967,002.

(60) Provisional application No. 62/088,035, filed on Dec. 5, 2014.

(51) Int. Cl.
A23K 20/174 (2016.01)
A23K 20/00 (2016.01)
A23K 20/24 (2016.01)
A23K 50/30 (2016.01)
A23K 50/60 (2016.01)
A61K 9/00 (2006.01)
A61K 33/06 (2006.01)

(52) U.S. Cl.
CPC .............. A61K 33/06 (2013.01); A23K 20/00 (2016.05); A23K 20/174 (2016.05); A23K 20/24 (2016.05); A23K 50/30 (2016.05); A23K 50/60 (2016.05); A61K 9/0056 (2013.01)

(58) Field of Classification Search
None
See application file for complete search history.

(56) References Cited

U.S. PATENT DOCUMENTS

| 3,639,584 | A | 2/1972 | Klenholz | |
| 3,666,488 | A | 5/1972 | Yukihiro | |
| 6,514,521 | B1 | 2/2003 | Julien | |
| 7,105,191 | B2 | 9/2006 | Mishra | |
| 8,303,979 | B2* | 11/2012 | van der Lende | A23K 20/147 514/567 |
| 8,771,723 | B2 | 7/2014 | Perdok | |
| 11,547,126 | B2 | 1/2023 | Ascensao | |
| 2004/0234626 | A1 | 11/2004 | Gardiner | |
| 2004/0234650 | A1* | 11/2004 | Mishra | A23K 20/105 426/74 |
| 2006/0257537 | A1 | 11/2006 | Claus | |
| 2011/0313043 | A1 | 12/2011 | Kramer | |
| 2014/0099406 | A1 | 4/2014 | Hoffmann Pegoraro | |
| 2014/0227396 | A1* | 8/2014 | Marcussen | A23K 40/20 426/61 |
| 2017/0088477 | A1 | 3/2017 | Morash | |

FOREIGN PATENT DOCUMENTS

| AU | 2013264002 | B2 | 11/2016 | |
| CN | 103931907 | A | 7/2014 | |
| DE | 102007020378 | A1 | 11/2008 | |
| KR | 20030065463 | A | 8/2003 | |
| KR | 20040093151 | A | 11/2004 | |
| KR | 20140033097 | A | 3/2014 | |
| KR | 20160047787 | A * | 5/2016 | ............. Y02P 60/22 |
| WO | 2002013982 | A1 | 2/2002 | |
| WO | 2003077672 | A1 | 9/2003 | |
| WO | WO-03077672 | A1 * | 9/2003 | ........... A23K 20/105 |
| WO | 2012159186 | A1 | 11/2012 | |
| WO | 2016090366 | A1 | 6/2016 | |
| WO | 2016177891 | A2 | 11/2016 | |

OTHER PUBLICATIONS

Lundberg et al. "Nitrate and nitrite in biology, nutrition and therapeutics", Nature Chemical Biology vol. 5 No. 12, Dec. 2009 (Year: 2009).*
(Lidder, S et al.) Vascular Effects of Dietary Nitrate (As Found in Green Leafy Vegetables and Beetroot) Via The Nitrate-Nitrite-Nitric Oxide Pathway. British Journal of Clinical Pharmacology. 2012. vol. 75, No. 3; p. 677.
(Stahl, C) Research Spotlight. Swine News NC State University. Sep. 2008. vol. 31, No. 9, [Retrieved on Jan. 15, 2016]. Retrieved from the internet; URL: <https://www.ncsu.edu/project/swine_extension/swine_news/2008/september/september_08.pdf>.
(Wu, G et al.) Important Roles for the Arginine Family of Amino Acids in Swine Nutrition and Production. Livestock Science. 2007. vol. 112.
Alonso-Spilsbury, Maria et al., Perinatal asphyxia pathophysiology in pig and human: A review. Animal reproduction science 90 (2005) 1-30.
Brotanek, Vladimir, M.D., et al., "Changes in uterine blood flow during uterine contractions", Am. J. Obstet. Gynecol. 103:8; 1108 (1969).

(Continued)

Primary Examiner — Susan T Tran

(57) ABSTRACT

A premix is disclosed. The premix includes a nitrate compound and salts thereof in the amount of greater than about 50% by weight of the premix. The premix also includes vitamins and trace minerals. The premix is formulated for use in at least one of a gestation or lactation phase of an animal and in an amount of less than about five percent by weight (5.0 wt %) inclusion per metric ton of the premix. A supplement for an animal feed for feeding during at least one of an animal's gestation phase and/or lactation phase is also disclosed. A method for feeding an animal is also disclosed.

13 Claims, No Drawings

(56) References Cited

OTHER PUBLICATIONS

Dantzer, Vibeke, "Electron microscopy of the initial stages of placentation in the pig", Anat Embryol (1985), 172:281-293.
Dougall, Hamish T., et al., "The effect of amoxycillin on salivary nitrite concentrations: an important mechanism of adverse reactions?" Br J Clin Pharmac 1995; 39:460-462.
Duncan, Callum, et al., "Chemical generation of nitric oxide in the mouth from the enterosalivary circulation of dietary nitrate", Nat Med 1:6; 546-551, Jun. 1995.
Dyck, G., et al., "Causes of Piglet Death From Bith To Weaning", Can J. Anim. Sci. 67: 543-547 (Jun. 1987).
Feng, Zhanyu et al. "Application of an N-Carbamylglutamate, arginine endogenous activator, in Swine production", Swine Production, No. 4, pp. 9-11 (Year: 2010).
Fraser, David, et al. "Farrowing behaviour and stillbirth in two environments: an evaluation of the restraint-stillbirth hypothesis", Applied Animal Behaviour Science 55 (1997) 51-66.
Friend, D. W., et al. "the Duration of Farrowing in Relation to the Reproductive Performance of Yorkshire Sows", Can. J. Comp. Med. Vet. Sci., vol. 26, Jun. 1962, pp. 127-130.
Gagnon, Robert, "Placental insufficiency and its consequences", European Journal of Obstetrics & Gynecology and Reproductive Biology, 110 (2003) S99-S107.
Govoni, Micro, et al., "The increase in plasma nitrite after a dietary nitrate load is markedly attenuated by an antibacterial mouthwash", Nitric Oxide 19 (2008) 333-337.
Henriksen, Tore, et al., "The fetal origins hypothesis: placental insufficiency and inheritance versus maternal malnutrition in well-nourished populations", Acta Obstet Gynecol Scand 2002: 81: 112-114.
Jansson, Emmelie A., et al., "A mammalian functional nitrate reductase that regulates nitrite and nitric oxide homeostasis", Nat Chem Biol 4:7 (Jul. 2008) 411-417.
Kilbride, A. L., et al., "A cohort study of preweaning piglet mortality and farrowing accommodation on 112 commercial pig farms in England", Preventive Veterinary Medicine 104 (2012) 281-291.
Kim, Sung Woo, et al., "Regulatory role for amino acids in mammary gland growth and milk synthesis", Amino Acids (2009) 37:89-95.
Le Cozler, Yannick, et al., "Factors associated with stillborn and mummified piglets in high-prolific sows", Animal Research, EDP Sciences, 2002, 51(3), pp. 261-268.
Li, Yuzhi, et al., "Pre-weaning mortality of piglets in a bedded group-farrowing system", J of Swine Health Prod. 2010; 18(2): 75-80.
Mainau, E., et al., "A behavioural scale to measure ease of farrowing in sows", Theriogenology 74 (2010) 1279-1287.
Marchant, J. N., et al., "Timing and causes of piglet mortality in alternative and confarrowing systems", Veterinary Record (2000) 147, 209-214.
Mateo, R. D., et al., "Effects of dietary arginine supplementation during gestation and lactation on the performance of lactating primiparous sows and nursing piglets", J Anim Sci 2008, 86:827-835.
Modesto, M. et al. Strategies to augment non-immune system based defence mechanisms against gastrointestinal diseases in pigs. NJAS-Wageningen Journal of Life Sciences, v. 58, n. 3-4, p. 149-156, 2011.
Oliviero, Claudio, et al., "Environmental and sow-related factors affecting the duration of farrowing", Animal Reproduction Science 119 (2010) 85-91.
Pernoll, M. L., and Benson R. C. (Ed.). 1988. Current Obstetric and Gynecological Diagnosis and Treatment (6th Ed.). Appleton and Lange, Nonvalk, CT.
Perry, J. S., "The mammalian fetal membranes", J. Reprod. Fert. (1981) 62, 321-335.
Persson, E. 1996. Studies of the endometrium and placenta during early pregnancy in the pig. Publisher: SLU, Uppsala (Sweden).
Randall, G. C.B., et al., "Observations on parturition in the sow. II. Factors influencing stillbirth and perinatal mortality", Vet. Rec. (1972) 90:183-186.
Rhodes, P. M., et al., "The L-Arginine:Nitric Oxide Pathway is the Major Source of Plasma Nitrite in Fasted Humans", Biochemical and Biophysical Research Communications, vol. 209, No. 2, 1995 (Apr. 17, 1995), pp. 590-596.
Seerley, R. W et al. Effect of nitrate or nitrite administered continuously in drinking water for swine and sheep. Journal of Animal Science, v. 24, n. 4, p. 1014-10119, 1965.
Senger, P. L., Pathways to pregnancy and parturition, "Placentas have different distributions of chorionic villi", Chapter 14, p. 306, 2005.
Thomas, Douglas D., et al., "The biological lifetime of nitric oxide: Implications for the perivascular dynamics of NO and O2", Proceedings of the National Academy of Science, Jan. 2, 2001, vol. 98, No. 1, pp. 355-360.
Tucker, T. M., et al., "Intrapartum Assessment of Fetal Well-Being", Clin. Obstet. & Gynecol. 33515. 1990. pp. 515-252.
Webb, Andrew J., et al., "Acute blood pressure lowering, vasoprotective and anti-platelet properties of dietary nitrate via bioconversion to nitrite", Hypertension. Mar. 2008 ; 51(3): 784-790. doi:10.1161/HYPERTENSIONAHA.107.103523.
Wu, Guoyao, et al., "Impacts of arginine nutrition on embryonic and fetal development in mammals", Amino Acids (2013) 45:241-256.
Zhai Xiao-ju et al., "Advances in Using Nitride in Preventing Myocardial Ischemic-Reperfusion Injury", Adv Cardiovasc Dis, vol. 32, No. 4, pp. 582-586, published in Jul. 2011.
AASV, Basic Pig Terms, (2012), AASV, pp. 1-11 (Year: 2012).
Baxter, E.M. et al., "Investigating the behavioural and physiological indicators of neonatal survival in pigs", Theriogenology 69 (2008 )773-783.
Bouwkamp, et al., "Verslag van een onderzoek naar de gevolgen van extra nitraattoevoeging aan drinkwater voor mestvarkens en gespeende biggen" [Effects of increased concentrations of nitrate in drinking water of fattening pigs and weaned piglets] 1988, Tijdschr Diergeneesk 113 (13), 737-747.
Bruckdorfer, Richard "The basics about nitric oxide", Molecula Aspects of Medicine 26 (2005) 3-31.
Froning et al: Color of Poultry Meat as Influenced by Dietary Nitrates and Nitrites, Poultry Science, vol. 48, No. 2, Mar. 1, 1969 (Mar. 1, 1969), pp. 668-674, XP055765517, Oxford ISSN: 0032-5791, DOI: 10.3382/ps.0480668.
Gemma Vilahur et al., "Polyphenol-enriched Diet Prevents Coronary Endothelial Dysfunction by Activating the Akt/eNOS Pathway", Rev Esp Cardiol. 2015;68(3):216-225.
Ghasemi, "Review article: Quantitative Aspects of Nitric Oxide Production From Nitrate and Nitrite", EXCLI Journal 2022;21:470-486—ISSN 1661-2156.
Jaturasitha et al., "The Effect of Gender of Finishing Pigs Slaughtered at 110 Kilograms on Performance, and Carcass and Meat Quality", ScienceAsia 32 (2006): 297-305.
Kelm "Nitric oxide metabolism and breakdown", Biochimica et Biophysica Acta 1411 (1999) 273-289.
Larsen et al. "Dietary nitrate reduces resting metabolic rate: a randomized, crossover study in humans1-3", Am J Clin Nutr 2014;99:843-50.
Lundberg, Jon et al., "The nitrate-nitrite-nitric oxide pathway in physiology and therapeutics", Nature Reviews Drug Discovery, vol. 7 Issue 2, Feb. 2008 (Feb. 2008), DOI:10.1038/nrd2466.
Lundberg, Jon O. et al., "Nitrate and nitrite in biology, nutrition and therapeutics", Nature Chemical Biology, vol. 5, No. 12, Dec. 2009, pp. 865-869.
Pawlak-Chaouch et al., "Effect of dietary nitrate supplementation on metabolic rate during rest and exercise in human: A systematic review and a meta-analysis", Nitric Oxide 53 (2016) 65-76.
Penuela S. et al., "Characterization of embryonic mortality in broilers", Rev.MVZ Cordoba, 23(1):6500-6513, 2018. ISSN: 0122-0268.
Rocha et al., "A shortcut to wide-ranging biological actions of dietary polyphenols: modulation of the nitrate-nitrite-nitric oxide pathway in the gut", Food Funct., 2014, 5, 1646-1652.

(56) References Cited

OTHER PUBLICATIONS

Seideman, S.C., et al., "Factors associated with fresh meat color: a review", Journal of Food Quality 6.3 (Feb. 15, 1984): 211-237.
Siervo, et al., "Intentional weight loss in overweight and obese individuals and cognitive function: a systematic review and meta-analysis", International Association for the Study of Obesity, 12, 968-983, 2011.
Umans and Levi, "Nitric Oxide in the Regulation of Blood Flow and Arterial Pressure", Annu. Rev. Physiol. 1995. 57:771-90.
Wu Qi, Carbon monoxide—an important biologically active molecule, Chemistry, Issue 5, Dec. 31, 1998, 38-43 [English translation included].
Yaping, et al., Antihypertensive effect mediated by nitrite and its mechanism, Science Bulletin, vol. 47, Issue 1, Jan. 31, 2002, 41-43. [English translation included].
Bosi et al., "Effect of dietary addition of nitrateon growth, salivary and gastric function,immune response, and excretionof *Salmonella enterica* serovarTyphimurium, in weaning pigs challengedwith this microbe strain", Italian Journal of Animal Science,, vol. 6, No. Suppl. 1, Jan. 1, 2007 (Jan. 1, 2007), pp. 266-268.
Trevisi et al., "Effect of high oral doses of nitrate on salivary recirculation of nitrates and nitrites and on bacterial diversity in the saliva of young pigs : Oral nitrate, salivary nitrate and microbiota", Journal of Animal Physiology and Animal Nutrition. , vol. 95, No. 2, Aug. 27, 2010 (Aug. 27, 2010), pp. 206-213.

\* cited by examiner

ANIMAL FEED SUPPLEMENT AND METHOD

CROSS REFERENCE TO RELATED APPLICATION

This application is a Divisional of U.S. patent application Ser. No. 15/533,120, filed Jun. 5, 2017, and entitled ANIMAL FEED SUPPLEMENT AND METHOD, which is a national phase application of PCT/US2015/064293, filed Dec. 7, 2015, and entitled ANIMAL FEED SUPPLEMENT AND METHOD, which claims the benefit of the U.S. Provisional Patent Application No. 62/088,035, filed Dec. 5, 2014, and entitled ANIMAL FEED SUPPLEMENT AND METHOD, each of which is hereby incorporated by reference in its entirety.

BACKGROUND

Feeding calcium nitrate and other ingredients to ruminants is one way to mitigate methane production. For example, U.S. Pat. No. 8,771,723 titled "Compositions For Reducing Gastro-Intestinal Methanogenesis In Ruminants" issued to Hindrik Bene Perdok et al. and assigned to CAN Technologies, Inc. discloses one such method. But such method feeds ruminants the calcium nitrate and other ingredients for the purpose of hydrogen gas removal in the rumen of the ruminant.

It is also known to feed to gestating sows a product enriched in L-arginine. One such known method is described in PCT Patent Application Publication No. WO 03/009703A1 titled "Dietary Modifications To Improve Fertility" filed by Tette Van der Leande and assigned to Nutreco Netherland B.V. However, such known method is directed to feeding gestating sows the L-arginine for the purpose of improving fertility of pigs by improvement of placentation in the pig (e.g. decreasing embryonic and fetal mortality in the placenta).

Accordingly, it would be advantageous to provide a feed for an animal for increasing vasodilatation of the animal during gestation and lactation phases.

SUMMARY

The present invention is directed to an animal feed containing a nitric oxide producing compound. In one aspect, the nitric oxide producing compound is at least one of calcium nitrite, magnesium nitrite or salts thereof. The nitric oxide producing compound may be introduced into the animal feed through a premix, for example, which can be further incorporated into the animal feed product. A supplement containing a nitric acid producing compound is also contemplated by the present invention. The present invention is further directed to a method of supplying an animal such animal feed or supplement containing the nitric oxide producing compound. In one aspect of the present invention, the animal feed or supplement containing the nitric oxide producing compound is supplied during at least one of a gestation feed or lactation feed. In a particular aspect of the present invention, the animal feed or supplement containing the nitric oxide producing compound is supplied during at least one of a gestation feed or lactation feed through a liquid application in an amount less than 90 grams of nitric oxide producing compound per animal per day. The present invention is also directed at the use of a nitric oxide producing compound in animal feed to increase vasodilation of the placenta and the mammary glands of the animal. The present invention may also be directed to the use of a nitric oxide producing compound in animal feed to increase systemic vasodilation for the reduction of animal fatigue and farrowing time. In one aspect, the present invention involves a premix. In this aspect, the premix includes a nitrate compound and salts thereof in the amount of greater than about 50% by weight of the premix. The premix may also include vitamins and trace minerals. The premix may be formulated for use in at least one of a number of phases of swine production including the gestation or lactation phase of an animal and in an amount of less than about five percent by weight (5.0 wt %) inclusion per metric ton of the premix.

In a further aspect, the present invention involves a supplement for an animal feed for feeding during at least one of an animal's gestation phase and/or lactation phase. In this aspect, the supplement may include a nitric oxide producing compound in an amount of less than 10 kg/metric ton of the total weight of the feed.

In yet another aspect, the present invention involves a method for feeding an animal. The method includes providing to the animal an animal feed product containing at least one of gestation feed and a lactation feed having a nitric oxide producing compound in an amount of less than 10 kg/metric ton of the total weight of the feed. The method also includes providing the feed to the animal 110 days after gestation of the animal.

DETAILED DESCRIPTION

Specific details of several embodiments of the disclosure are described below with reference to an animal feed supplement. The animal feed supplement is intended for feeding to a non-ruminant animal, such as a monogastric animal, for example, a sow.

Swine Production Stages

Breeding and Gestation. Swine production can be logically separated into a number of phases, beginning with the sow being bred. The sow is bred during her estrous period. In the phase between weaning the sow and breeding, a special breeding feed can be fed to the sow. After breeding, the sow "gestates" her litter for 113 to 116 days before the piglets are born or "farrowed." As used in this disclosure, the term "gestation" or gestation phase means the 113 to 116 day period when the sow is pregnant from breeding until farrowing.

Farrowing. The process of giving birth is called farrowing. Sows are normally moved into a farrowing room a few days prior to farrowing and remain in this location through lactation. In certain instances, sows are moved into a farrowing room five to seven days prior to farrowing. Sows typically farrow from eight to fourteen piglets, which as a group are called a litter. It is also possible for sows to farrow from eight to eighteen piglets, which as a group are also called a litter. The piglets are born weighing about three pounds at birth. As used in this disclosure, the term "farrowing" means birth, and the term "farrowing phase" means the period from birth to weaning. The period of time called the transition period is typically seven days pre-farrowing until one to five days post farrowing. The piglets stay with the lactating sow for about 19-35 days after farrowing, during which time the piglets drink milk produced by the lactating sow. As used in this disclosure, the term "lactating," lactation, or lactation phase means the period when a sow is producing milk and providing the milk to her piglets and the period of time from farrowing until weaning is called the lactation period. During these periods a farm can provide one feed (typically called a lactation feed) or two feeds (typically a transition feed and a lactation feed).

Weaning. The piglets are weaned from the sow at anywhere from five days to five weeks, with most operations weaning pigs at two to four weeks after farrowing. As used in this disclosure, the term "weaning" means the process of removing the piglets from the sow and moving them to the nursery. During a weaning or nursery phase, the piglets remain in the nursery (est. until 42 days after farrowing).

Growing and Finishing. Pigs are normally removed from the nursery after the weaning (or nursery) phase and placed in a grow-finishing building until they reach market weight.

Swine Production Diets

During the gestation phase, the sow is typically fed a gestation diet. A gestation diet is characterized primarily by its time of feeding. The gestation diet is provided in fixed daily amounts to achieve targeted nutrient intakes. See TABLE 1. On about day 110 of the gestation phase, or when the sow is moved into farrowing, the sow is typically switched to a fixed amount of lactation feed. A lactation feed is characterized primarily by the time of feeding and contains the appropriate nutrients and energy to support milk production. See TABLE 1. During the lactation phase, the sow is fed a lactation feed ad libitum or in fixed daily amounts. After the lactation phase, the sow is separated from its piglets (the weaning phase for the piglets) and the sow enters rebreeding.

During the gestation phase, the fetus receives nutrients from the placenta of the sow. During the lactation phase, the piglets receive nutrients from the milk produced by the sow. During the nursery phase, the piglets are fed a nursery diet. A weaning diet is characterized by the time of feeding, which begins at the time of weaning and end at approximately 25-35 kg body weight of the piglet.

Animal Feed Supplement

The monogastric animal is fed a supplement that is included in an animal feed during at least one of the gestation and lactation phases according to an exemplary embodiment. For instance, the monogastric animal is fed a supplement that is included in at least one of a breeding feed or transition feed. The animal feed supplement of the present invention comprises a nitrate compound, typically a physiologically acceptable or tolerated nitrate compound. The nitrate compound has sufficient solubility in water according to a preferred embodiment. The nitrate compound is an ionic nitrate compound according to preferred embodiments, most preferably an inorganic nitrate salt. Exemplary salts include sodium nitrate, potassium nitrate, calcium nitrate, or ammonium nitrate, all of which are readily soluble in water at standard temperature and pressure. In another aspect, exemplary salts include sodium nitrate, potassium nitrate, calcium nitrate, magnesium nitrate, ammonium nitrate, or a combination thereof, all of which are readily soluble in water at standard temperature and pressure. In a particular aspect, the salt is a magnesium nitrate. The salts can include different hydrated forms. The salts can also include double salts (e.g. calcium nitrate and ammonium nitrate).

According to an exemplary embodiment, the nitrate is provided as inorganic calcium nitrate having the formula $Ca(NO_3)_2$. Calcium nitrate is also referred to as calcium dinitrate, Kalksalpeter, nitrocalcite, Norwegian saltpeter, and lime nitrate. Calcium nitrate may be produced by treating limestone with nitric acid, followed by neutralization with ammonia according to the reaction: $CaCO_3 + 2HNO_3 \rightarrow Ca(NO_3)_2 + CO_2 + H_2O$. In another exemplary embodiment, the nitrate is provided as an inorganic salt of magnesium nitrate hexahydrate having the formula $(Mg(NO_3)_2*6H_2O)$. This product contains 10.8% N from nitrate and 9.5% Magnesium.

A variety of related complex inorganic salts of calcium nitrate include calcium ammonium nitrate decahydrate and calcium potassium nitrate decahydrate. Calcium ammonium nitrate is a double salt (calcium nitrate and ammonium nitrate) having the formula $5Ca(NO_3)_2*NH_4NO_3*10H_2O$. According to an exemplary embodiment, the calcium ammonium nitrate is pentacalcium ammonium nitrate decahydrate commercially available from Bri-Chem Supply Limited with the following specification: Ammonium-N ($NH_4$—N) 1.1%; Nitrate-N($NO_3$—N): 14.4%; Total N: 15.5%; Calcium (Ca): 18.8%. According to another exemplary embodiment, the calcium nitrate is BOLIFOR CNF calcium nitrate feed grade having the formula $5Ca(NO_3)_2*NH_4NO_3*10H_2O$ commercially available from Yara Phosphates Oy of Helsingborg Sweden. According to an exemplary embodiment, the calcium nitrate can have the following specification: Calcium (Ca): 18.9%; Nitrogen (N) 15.5%; pH (10% solution): 6; bulk density kg/m3: 1050; appearance: prilled; size: <1.0 mm: 2%; 1.0-2.0 mm: 78%; >2 mm: 20%. Exemplary formulations of calcium nitrate lacking ammonia include $Ca(NO_3)_2*4H_2O$. An exemplary anhydrous air-stable derivative of calcium nitrate includes the urea complex $Ca(NO_3)_2*4[OC(NH_2)_2]$.

The nitrate may be provided by a variety of plant ingredients according to alternative embodiments. Such plant ingredients may include, for example, leafy greens such as spinach, arugula and beetroot. Beetroot has an inorganic nitrate content typically ranging from 110 to 3670 mg nitrate/kg.

The supplement including the nitrate compound may be fed to the sow such that the amount of nitrate fed per sow per day is from 90 grams to less than 0.5 grams. In a particular aspect, the supplement including the nitrate compound may be fed to the sow such that the amount of nitrate fed per sow per day is less than 10 g nitrate per sow per day, also for example, less than 5 g nitrate per sow per day, also for example, less than 4 g nitrate per sow per day, also for example, less than 3 g nitrate per sow per day, also for example, less than 2 g nitrate per sow per day also for example, less than 1 g nitrate per sow per day, also for example, less than 0.5 g nitrate per sow per day according to suitable embodiments.

The supplement including the nitrate compound may also be fed to the sow such that the amount of nitrate fed per sow per day is from 90 mg nitrate per kg of body weight of the sow to less than 5 mg nitrate per kg of body weight of the sow. In an exemplary aspect, the supplement including the nitrate compound may also be fed to the sow such that the amount of nitrate fed per sow per day is less than 35 mg nitrate per kg of body weight of the sow, also for example, less than 30 mg nitrate per kg of body weight of the sow, also for example, less than 25 mg nitrate per kg of body weight of the sow, also for example, less than 20 mg nitrate per kg of body weight of the sow, also for example, less than 15 mg nitrate per kg of body weight of the sow, also for example, less than 10 mg nitrate per kg of body weight of the sow, also for example, less than 5 mg nitrate per kg of body weight of the sow according to suitable embodiments. The amount of nitrate in the feed (and the amount of nitrite) may be measured via ion chromatography. According to the ion chromatography method, samples are extracted with water, filtered, diluted and then applied to an anion exchange column. Nitrate is separated and identified using isocratic carbonate/bicarbonate elution coupled with suppressed conductivity detection. Concentration is determined using a standard curve of known nitrate solutions.

The supplement including the nitrate compound may be included in a complete animal feed. The amount of calcium nitrate and its related salts in the complete feed is less than 1 wt % of the total weight of the feed, for example less than 0.5 wt %, also for example less than 0.4 wt %, also for example less than 0.3 wt %, also for example less than 0.2 wt %, also for example less than 0.1 wt %, also for example less than 0.09 wt %, also for example less than 0.08 wt %, also for example less than 0.07 wt %, also for example less than 0.06 wt %, also for example less than 0.05 wt % according to suitable embodiments.

The supplement comprising the nitrate compound may be included in a premix feed. In certain aspects, the premix feed is then added to an animal feed and provided to the animal (e.g. sow) such that the amount of nitrate fed per animal per day is from 90 mg nitrate per kg of body weight of the sow to less than 5 mg nitrate per kg of body weight of the animal. The amount of calcium nitrate and its related salts in the premix feed is greater than 50 wt % of the total weight of the feed, for example, greater than 60 wt %, also for example, greater than 70 wt %, also for example, greater than 80 wt %, also for example, greater than 90 wt %, also for example, greater than 95 wt % according to suitable embodiments.

Nitrate-Nitrite-NO Pathway

Without intending to be limited to any particular theory, it is believed the nitrate in the supplement is a source for the biological messenger nitric oxide (NO) according to a non-enzymatic pathway for the generation of NO (nitrate-nitrite-NO pathway). Unlike arginine conversion to nitric oxide, nitrate conversion to nitric oxide via the nitrate-nitrite-NO pathway is not dependent upon oxygen levels. During the farrowing process, sows may experience fatigue and periods of hypoxia or lower oxygen levels.

It is believed the release of NO in the animal is important for the control of vascular tone, smooth muscle growth, platelet aggregation and inflammation. The release of NO in the animal, for example, in a sow fed the supplement, is believed to induce vasodilation and increased blood flow and exchange of oxygen.

In one aspect of the present invention is a method of supplying an animal (e.g. a sow) a NO producing compound in at least one of a gestation or lactation feed through a liquid application such as drinking water. An exemplary dosage using this method is less than 90 grams of NO producing compound per animal per day.

Vasodilation

The term "vasodilation" (or vasodilatation) as used in this disclosure refers to the widening of blood vessels in the animal. Vasodilation results from relaxation of smooth muscle cells within the vessel walls, in particular in the large veins, large arteries, and smaller arterioles. When blood vessels dilate in the animal, the flow of blood is increased due to a decrease in vascular resistance. Vasodilation may be localized to a specific organ (depending on the metabolic needs of a particular tissue, as during stress), or it may be systemic (seen throughout the entire systemic circulation). The primary function of vasodilation is to increase blood flow in the body to tissues that need it most. This is often in response to a localized need of oxygen, but can occur when the tissue in question is not receiving enough glucose or lipids or other nutrients.

Without intending to be limited to any particular theory, it is believed the nitrate in the supplement produces NO when consumed by the animal, which causes vasodilation in specific organs of the animal during certain periods. For example, the animal feed supplement fed during gestation may result in vasodilation in the placenta—thereby increasing the exchange of oxygen and nutrients between the placenta and the fetus and further thereby decreasing the number of stillbirths. Also for example, the supplement fed during gestation through lactation may result in vasodilation of the placenta of the sow—thereby reducing stillborn births during farrowing. Also for example, the supplement fed during the gestation phase through the lactation phase may result in improved nutrient and oxygen delivery throughout the entire systemic circulation—thereby reducing stillborn births due to less sow fatigue and reducing farrowing time. Also for example, the supplement fed during the lactation phase may result in vasodilation of the mammary glands of the sow—thereby increasing milk production and further thereby reducing piglet mortality and increasing piglet vitality during the weaning phase.

Benefits of Supplement

Feeding the supplement during at least one of the gestation and lactation phases of swine production may result in certain physiological benefits to the sow and/or her offspring compared with not feeding the supplement. For example, a sow fed the supplement during the pre-farrowing phase may result in fewer stillborn piglets being born. Also for example, a sow fed the supplement during at least one of the lactation phase or weaning phase may result in piglets showing greater vitality and reduced mortality.

The number of total born piglets in a litter is determined during ovulation, insemination, and early gestation. The number of piglets born alive is determined by: (i) mortality in utero (mortality in early gestation results in fewer total born piglets while mortality in late gestation can result in an increased number of piglets born mummified); and (ii) mortality during the farrowing process (stillborn). Stillbirth can occur during gestation (Type I stillbirth), which is often due to an infectious cause, or intra-partum (Type II stillbirths), which is often non-infectious.

Total born piglets. Feeding the supplement including the nitrate compound to the animal (e.g. sow) during the gestation phase may promote embryo survival during implantation. As a result, an increase may be observed in the total number of offspring (e.g. piglets) born due to increased embryo survival during implantation. In sows, attachment of the placental membranes of the conceptus to the endometrium takes place 12 to 13 days after ovulation (initial attachment occurs at day 12 and is well established at day 18-20 after ovulation). After initial placental development, two important processes in creating a functional placenta are angiogenesis and vasculogenesis. These processes are essential for the embryo to take up nutrients such as amino acids, glucose and oxygen from the maternal bloodstream and to loose waste products, such as $CO_2$. Angiogenesis is the expansion of blood vessels from pre-existing vessels in the endometrium of the mother, while vasculogenesis is the formation of new blood vessels in the fetal membranes. When vascularization is not developed properly, problems can occur, one of them being placental insufficiency. Placental insufficiency is caused by a poor placentation (a poor vascular development at the utero-placental surface) and leads to a degenerating placental functioning and a decrease in exchange of oxygen and nutrients from placenta to fetus. As a result, the fetus will have a shortage of oxygen, or hypoxemia. Without intending to be limited to any particular theory, it is believed feeding the animal feed supplement to the sow during the gestation phase causes vasodilation to increases blood flow to the placenta during early gestation resulting in improved embryonic survival and implantation, further resulting in an increased number of total live born piglets and further having improved uniformity, birth weight and vitality. According to an exemplary embodiment, feeding the supplement to the sow during the gestation phase (including the transition phase) may result in vasodilation resulting in: (i) improved development of a functional placenta through increased angiogenesis and/or vasculogenesis; (ii) decreased placental insufficiency; and/or (iii) increased exchange of oxygen and nutrients from the placenta to the fetus.

Stillbirth. Feeding the animal feed supplement comprising the nitrate compound to the animal (e.g. sow) during the gestation phase may reduce the number of stillborn during farrowing. The major cause of stillbirths is asphyxiation. This is caused by the cumulative effects of successive contractions of the uterus, which result in reduced oxygenation of the unborn piglets. Reduced oxygenation (asphyxiation) results in piglet death in utero or results in reduced piglet vitality which is associated with a higher mortality risk during the first three days after farrowing. Asphyxiation is further complicated by the farrowing time, as increased farrowing time due to sow fatigue results in higher stillbirth piglets. Increased uterine contractions due to long farrowing times also increase the risk of damage, occlusion or rupture of the umbilical cord. Without intending to be limited to any particular theory, it is believed feeding the supplement to the sow during gestation through lactation phases causes vasodilation to increase blood flow to the placenta and therefore oxygen flow to the placenta during the farrowing process to support uterine contractions. Furthermore, systemic effects of feeding the supplement will reduce sow fatigue and reduce farrowing time. According to an exemplary embodiment, feeding supplement to the sow during the gestation through lactation phases may result in vasodilation resulting in: (i) decreased asphyxiation of the fetus; and/or (ii) reduced farrowing duration.

Reduced Piglet Post-Farrowing Mortality. Feeding the supplement including the nitrate compound to the animal (e.g. sow) during the lactation phase and/or transition phase may decrease or reduce piglet post-farrowing mortality. Without intending to be limited to any particular theory, it is believed the nitrate in the animal feed supplement produces nitric oxide which causes vasodilation of the mammary glands of the sow, thereby increasing milk production. Increased milk production by the sow results in increased uptake of colostrum and milk by the piglets in the litter during the first few days post-farrowing. Increased colostrum and milk uptake by the piglets leads to reduced mortality during the first week post-farrowing. Without intending to be limited to any particular theory, it is believed that the sow vitality can be improved resulting in less crushing of piglets and better start of feed intake in the early lactation phase.

Increased Piglet Gain and Vitality Post-Farrowing. Feeding the animal feed supplement including the nitrate compound to the animal (e.g. sow) during the lactation phase and/or transition phase may increase the growth and vitality of the piglet post farrowing. Without intending to be limited to any particular theory, it is believed the nitrate in the supplement produces nitric oxide which causes vasodilation of the mammary glands of the sow, thereby increasing milk production. Increased milk production by the sow results in increased uptake of milk by the piglets in the litter, and a greater average daily gain over the entire suckling period. Also for example, the piglets show increased vitality as demonstrated by reduced time from birth to first time suckling. Vitality is calculated as the amount of time from birth until nursing.

Other Benefits. In addition to the benefits of vasodilation from the nitrate in the supplement, the animal may receive additional benefits. Additional benefits from the supplement may include, for example, post weaning performance of piglets in gain, feed intake, efficiency, immunity, meat quality, gut health, color/bloom, ability to cope with heat stress, ear necroses, streptococcus. Other additional benefits may include, for example, an increased effect on feed intake, efficiency, udder quality, milk production, milk quality, incidence of lameness, heat stress and hair growth.

Animal Feed

The supplement refers to an additive or premix that includes a nitrate compound. The supplement may be added to an animal feed. The term "animal feed" as used in this disclosure means a feed ration produced for consumption by an animal.

The animal feed supplement may be included in a compound animal feed according to an exemplary embodiment. The term "compound feed" as used in this disclosure means an animal feed blended to include two or more ingredients which assist in meeting certain daily nutritional requirements of an animal. The animal feed may be a complete animal feed according to an exemplary embodiment. The term "complete feed" as used in this disclosure means an animal feed which is a complete feed, e.g. a nutritionally balanced blend of ingredients designed as the sole ration to provide all the daily nutritional requirements of an animal to maintain life and promote production without any additional substances being consumed except for water. The animal feed may also be a concentrate animal feed according to an exemplary embodiment. The term "concentrate feed" as used in this disclosure means an animal feed that typically includes a protein source blended with supplements or additives or vitamins, trace minerals, other micro ingredients, macro minerals, etc. to provide a part of the ration for the animal. The concentrate feed may be fed along with other ingredients (e.g., forages in ruminants). The animal feed may include a premix according to an alternative embodiment. As used in this disclosure, the term "premix" means a blend of primarily vitamins and/or minerals along with appropriate carriers in an amount of less than about five percent (5.0%) inclusion per ton of complete feed. The animal feed may also include a base mix according to an exemplary embodiment. The term "base mix" as used in this disclosure means a blend containing vitamins, trace minerals and/or other micro ingredients plus macro minerals such as calcium, phosphorus, sodium, magnesium and potassium, or vitamin or trace mineral in an amount of less than ten percent (10.0%) inclusion per ton of complete feed. The animal feed may be a feed "supplement." The term "additive" as used in this disclosure means an ingredient such as a protein source, salt, mineral, additive, or buffer that is added to an animal feed. An example of an additive includes calcium, zinc, manganese, copper, iodine, cobalt, selenium and other trace ingredients. The supplement may be top dressed, dissolved in a liquid such as drinking water or any other consumable liquid presented to the animal, etc. according to other alternative embodiments.

The term "animals" as used in this disclosure includes ruminant and monogastric animals. As used in this disclosure, the term "ruminant" means any mammal that has a multi-compartment stomach and is associated with digestion by regurgitation and repeated chewing of a bolus or cud. Such ruminant mammals include, but are not limited to, bovine animals such as buffalo, bison, and all cattle, including calves, steers, heifers, cows, and bulls. As used in this disclosure, the term "monogastric" means any organism having a simple single-chambered stomach. Such monogastric animals include, but are not limited to, porcine, equine, caprine, ovine, avian animals, seafood (aquaculture) animals. Porcine monogastric animals include, for example, feeder pigs and breeding pigs, including piglets, sows, gilts, barrows, and boars. While the description is primarily with reference to sows, it is not limited as such and should be understood that the disclosure is applicable to other monogastric and ruminant animals.

Nutrients

The animal feed is the vehicle to deliver nutrients to the animal There are six major classes of nutrients: carbohydrates, fats, proteins, vitamins, minerals, and water. These nutrient classes can be categorized as either macronutrients (needed in relatively large amounts) or micronutrients (needed in smaller quantities). The macronutrients are carbohydrates, fats, fiber, proteins, and water. The micronutrients are minerals and vitamins. The macronutrients (excluding water) provide structural material (amino acids from which proteins are built, and lipids from which cell membranes and some signaling molecules are built) and energy. Vitamins, minerals, fiber, and water do not provide energy, but are required for other reasons. Micronutrients include antioxidants and phytochemicals. Nutrients are delivered by sources of ingredients.

Macromineral (also referred to as bulk minerals) nutrients include, for example, calcium, chlorine (as chloride ions), magnesium, phosphorus, potassium, sodium, and sulfur. Micromineral (also referred to as trace minerals) nutrients include, for example, cobalt, copper, chromium, iodine, iron, manganese, molybdenum, nickel, selenium, vandadium, and zinc.

Vitamins nutrients include, for example, vitamin A Ingredient sources of vitamin A include, for example, vitamin A supplement, vitamin A oil, etc. Vitamins also include, for example, vitamin B1, vitamin B2, vitamin B3, vitamin B4, vitamin B5, vitamin B6, vitamin B7, vitamin B9, vitamin B12, and vitamin C Vitamins also include, for example, vitamin D Ingredient sources of vitamin D include, for example, vitamin D supplement. Vitamins also include, for example, vitamin E Ingredient sources of vitamin E include, for example, vitamin E supplement. Vitamins also include, for example, vitamin K. Other vitamin product ingredients may include, for example, riboflavin, vitamin D3 supplement, niacin, betaine, choline chloride, tocopherol, inositol, etc.

Ingredients

The animal feed may include a combination or compound of various ingredients to deliver the nutrients. Examples of ingredients include protein ingredients, grain products, grain by-products, roughage products, fats, minerals, vitamins, additives or other ingredients according to an exemplary embodiment. Protein ingredients may include, for example, animal derived proteins such as: dried blood meal, meat meal, meat and bone meal, poultry by-product meal, hydrolyzed feather meal, etc. Protein ingredients may also include, for example, marine products such as: fish meal, crab meal, shrimp meal, condensed fish solubles, fish protein concentrate, etc. Protein ingredients may further include, for example, plant products such as: algae meal, beans, coconut meal, cottonseed meal, rapeseed meal, canola meal, linseed meal, peanut meal, soybean meal, sunflower meal, peas, soy protein concentrate, dried yeast, active dried yeast, etc. Protein ingredients may also include, for example, milk products such as: dried skim milk, condensed skim milk, dried whey, condensed whey, dried hydrolyzed whey, casein, dried whole milk, dried milk protein, dried hydrolyzed casein, etc. Grain product ingredients may include, for example, corn, milo, oats, rice, rye, wheat, etc. Grain by-product ingredients may also include, for example, corn bran, peanut skins, rice bran, brewers dried grains, distillers dried grains, distillers dried grains with solubles, corn gluten feed, corn gluten meal, corn germ meal, flour, oat groats, hominy feed, corn flour, soy flour, malt sprouts, rye middlings, wheat middlings, wheat mill run, wheat shorts, wheat red dog, feeding oat meal, etc. Grain product ingredients may also include, for example high-moisture processed grain by-products. Such high-moisture processed grain by-products result from the processing of a number of different grains such as corn, wheat, and milo. Examples of high-moisture processed grain by-products include, without limitation, gluten, non-grain feed ingredients (e.g., molasses, beet pulp and other crop residues), and wet distiller's grain. Roughage product ingredients may include, for example, corn cob fractions, barley hulls, barley mill product, malt hulls, cottonseed hulls, almond hulls, sunflower hulls, oat hulls, peanut hulls, rice mill byproduct, bagasse, soybean hulls, soybean mill feed, dried citrus pulp, dried citrus meal, dried apple pomace, dried tomato pomace, straw, hay, etc. Fat product ingredients may include, for example, beef fat, poultry fat, pork fat, restaurant grease, soy oil, corn oil, tallow, hydrolyzed animal fat, hydrolyzed vegetable fat, calcium salts of long chain fatty acids, hydrogenated glycerides, etc. Mineral product ingredients may include, for example, basic copper chloride, bone ash, bone meal, calcium acetate, calcium carbonate, calcium chloride, calcium gluconate, calcium hydroxide, calcium iodate, calcium iodobehenate, calcium oxide, calcium sulfate (anhydrous or dihydrate), cobalt acetate, cobalt carbonate, cobalt chloride, cobalt oxide, cobalt sulfate, copper carbonate, copper chloride, copper gluconate, copper hydroxide, copper orthophosphate, copper oxide, copper pyrophosphate, copper sulfate, cuprous iodide, dicalcium phosphate, diiodosalicylic acid, disodium phosphate, ethylenediamine dihydroiodide, ferrous fumarate, iron ammonium citrate, iron carbonate iron chloride, iron gluconate, iron oxide, iron phosphate, iron pyrophosphate, iron sulfate, reduced iron, magnesium acetate, magnesium carbonate, magnesium oxide, magnesium sulfate, manganese acetate, manganese carbonate, manganese chloride, manganese citrate (soluble), manganese gluconate, manganese orthophosphate, manganese oxide, manganese phosphate (dibasic), manganese sulfate, monocalcium phosphate, monosodium phosphate, dicalcium phosphate, phosphate deflourinated, rock phosphate, potassium acetate, potassium bicarbonate, potassium carbonate, potassium chloride, potassium iodate, potassium iodide, potassium, sulfate sodium acetate, sodium chloride, sodium bicarbonate, sodium iodate, sodium iodide, sodium sulfate, sodium, sodium sesquincarbonate, selenium, sulfur, thymol iodide, tricalcium phosphate, tripolyphosphate, zinc acetate, zinc carbonate, zinc chloride, zinc oxide, zinc sulfate, etc.

Vitamin product ingredients may include, for example, vitamin A supplement, vitamin A oil, vitamin D, vitamin B12 supplement, vitamin E supplement, riboflavin, vitamin D3 supplement, niacin, betaine, choline chloride, tocopherol, inositol, etc. Additive product ingredients can be used, for example, to protect animals from disease and/or stress (e.g. antibiotics, probiotics, etc.) and/or to stimulate or control growth and behavior (e.g. hormones).

Feed additives can be used, for example, to help provide a balanced diet (e.g., vitamins and/or trace minerals), to protect the animals from disease and/or stress (e.g., antibiotics, probiotics) and/or to stimulate or control growth and behavior (e.g., hormones). Additive product ingredients may include, for example: growth promoters, medicinal substances, buffers, antioxidants, enzymes, preservatives, pellet-binding agents, direct-fed microbials, etc. Additive product ingredients may also include, for example, ionophores (e.g. monesin, lasalocid, laidlomycin, etc.), β-agonist (zilpaterol, ractompamine, etc.), antibiotics (e.g., chlortetracycline (CTC), oxytetracycline, bacitrain, tylosin, aureomycin), probiotics and yeast cultures, coccidiostats (e.g., amprollium, decoquinate, lasalocid, monensin), and hormones (e.g., growth hormones or hormones that inhibit estrus and/or ovulation such as melengestrol acetate), pheromones, nutraceuticals, pharmaceuticals, flavanoids, nutritive and non-nutritive supplements, detoxicants, etc.

Examples of a feed used in gestation and lactation to which the supplement may be added is shown in TABLE 1 and TABLE 2.

TABLE 1

Gestation and Lactation Feed

|  | Gestation | Lactation |
| --- | --- | --- |
| PROTEIN | 14.0 (wt %) | 18.0 (wt %) |
| FAT | 4.5 (wt %) | 6.0 (wt %) |
| MOISTURE | 12.0 (wt %) | 12.0 (wt %) |
| FIBER | 7.0 (wt %) | 5.0 (wt %) |
| CALCIUM | 0.8 (wt %) | 1.0 (wt %) |
| PHOS | 0.5 (wt %) | 0.7 (wt %) |
| NET ENERGY | 2000 KCAL | 2200 KCAL |
| LYSINE | 0.6 (wt %) | 0.9 (wt %) |

TABLE 2

Gestation and Lactation Feed

|  | Gestation | Lactation |
| --- | --- | --- |
| PROTEIN | 15.0 (wt %) | 24.0 (wt %) |
| FAT | 6.0 (wt %) | 6.0 (wt %) |
| MOISTURE | 12.0 (wt %) | 12.0 (wt %) |
| FIBER | 5.0 (wt %) | 3.2 (wt %) |
| CALCIUM | 0.90 (wt %) | 0.90 (wt %) |
| PHOS | 0.70 (wt %) | 0.60 (wt %) |
| NET ENERGY | 2000 KCAL | 2200 KCAL |
| LYSINE | 0.506807 (wt %) | 0.90 (wt %) |

Example 1

Example 1 determines the effect of calcium nitrate in the diet of a sow. The sows entered a farrowing room on average on day 111 of gestation and received a standard lactation diet (see TABLE 1A and TABLE 1B) without (negative control) or with (positive control) the 1.0 kg/metric ton BOLIFOR CNF inorganic feed material of calcium nitrate feed grade (calcium nitrate, containing 63.1% of nitrate) commercially available from Yara Phosphates Oy of Helsingborg, Sweden. During lactation, sows were fed either the positive control or negative control standard lactation diet according to a step-up feeding schedule. Until farrowing the sows were fed a fixed amount of either the positive or negative controls of the standard lactation diet twice a day. After farrowing the amount of feed either the positive or negative controls of the standard lactation diet fed was increased gradually till a maximum of 8 kg/sow per day. The amount of which could be adjusted based on the appetite of the sow. Piglets were fed Ad libitum (no milk was provided other than from the sow a commercial creep feed (meal, dry) from day 4-16 of age and a pelleted commercial prestarter from day 16 till weaning. In total, 150 sows were allocated over the three rooms based on parity. Within 2 days after farrowing, litters were standardized to 13-14 piglets per sow.

TABLE 1A

| Ingredients | Positive Control (wt %) | Negative Control (wt %) |
| --- | --- | --- |
| Bolifor (calcium nitrate) | 0.1 | 0 |
| Natuphos m2346 0.75% | 0.75 | 0.75 |
| Wheat Midds By-Product 27-34% NDF | 17 | 17 |
| Canola Meal-00 RSM | 2.5 | 2.5 |
| Barley | 10 | 10 |
| Maize (bulk) | 19.534 | 19.347 |
| Wheat | 17.076 | 17.177 |
| Sunflower Meal 35% Protein | 1.5 | 1.5 |
| Soybean Hulls | 1.5 | 1.5 |
| Zeug Ad Lib 1% | 1 | 1 |
| Limestone powder | 1.423 | 1.373 |
| Monocalcium phosphate | 0.83 | 0.83 |
| Salt | 0.398 | 0.398 |
| L-Threonine | 0.053 | 0.053 |
| Soybean Meal-48% Protein | 8.405 | 8.412 |
| Fat-Palm Oil | 2.788 | 2.817 |
| Beet Pulp-Dry | 4.5 | 4.5 |
| Palm Kernel Meal-Expeller | 2.5 | 2.5 |
| Beet-Standard Molasses | 3.5 | 3.5 |
| Soybean-Gr FF heated (PL FD) | 4 | 4 |
| Fat-Fish Oil-Red Salmon | 0.5 | 0.5 |
| L-Lysine HCL | 0.243 | 0.243 |

TABLE 1B

| Nutrients | Units | Positive Control (wt %) | Negative Control (wt %) |
| --- | --- | --- | --- |
| Dry matter | % | 88.446 | 88.358 |
| Moisture | % | 11.554 | 11.642 |
| Protein | % | 15.846 | 15.846 |
| Fat | % | 6.315 | 6.338 |
| Ash | % | 6.124 | 6.074 |
| Fiber | % | 5.467 | 5.465 |
| Calcium | % | 0.857 | 0.838 |
| Phosphorus | % | 0.625 | 0.624 |
| Net energy | kcal | 2450 | 2450 |
| Lysine | % | 0.906 | 0.906 |

The following measurements were recorded as shown in TABLE 1C: (i) sow weight and backfat thickness when entering the farrowing room (day 111 of gestation) and at weaning (22 days post farrowing); (ii) sow reproductive performance was recorded right after farrowing (number of piglets born total, alive, stillborn, mummified); (iii) piglets weights were recorded at birth, day 5 after birth and at weaning; (iv) creep feed intake of piglets between day 4 and weaning was recorded; (v) number of piglets alive at day 4 and at weaning were registered; (vi) when piglets died, the reason for dying was also registered; and (vii) interventions during the birth process (e.g. the use of planate, oxytocin and birth assistance).

TABLE 1C

| Lactation (day 111-Weaning) | 1 Negative Control | 2 NC + 0.1% Bolifor CNF[1] | Pooled SEM | P Trt |
|---|---|---|---|---|
| Number of sows | 120 | 114 | — | — |
| Parity | 3.5 | 3.6 | — | — |
| Sow technical performance | | | | |
| Average day of gestation when entering farrowing room[2] | 111 | 111 | — | — |
| Average gestation length (days)[2] | 116 | 116 | — | — |
| Weight when entering the farrowing room (kg)[2] | 276.5 | 275.8 | — | — |
| Calculated weight at farrowing (kg) | 258.9 | 257.9 | 9.6 | 0.69 |
| Weight at weaning (kg)[3] | 243.9 | 243.1 | 10.2 | 0.72 |
| Weight change from farrowing-weaning (%)[3] | 7.2 | 7.1 | 1.1 | 0.77 |
| Backfat when entering the farrowing room (mm)[2] | 22.5 | 22.3 | — | — |
| Backfat at weaning (mm)[3] | 19.7 | 19.6 | 0.7 | 0.69 |
| Backfat change during lactation (%)[3] | 14.0 | 14.0 | 2.3 | 0.95 |
| Total feed intake during lactation (kg)[4] | 133.6 | 133.2 | 6.3 | 0.84 |
| ADFI during lactation (kg/sow/day)[4] | 6.0 | 6.0 | 0.2 | 0.91 |
| Sow reproductive performance | | | | |
| Lactation length (days)[2] | 21.6 | 21.7 | — | — |
| Total Born[2] | 16.5 | 16.3 | — | — |
| Total Born Alive[2] | 15.5 | 15.3 | — | — |
| Total Still Born[2] | 1.1 | 1.0 | — | — |
| Probability Born Alive (%)[8] | 93.3 | 93.8 | 1.4 | 0.51 |
| Probability Still Born (%)[8] | 6.7 | 6.2 | 1.4 | 0.51 |
| Probability Born Mummified (%) | 2.3 | 2.3 | 0.6 | 0.99 |
| Total number of piglets at the sow after cross fostering[2] | 13.5 | 13.5 | — | — |
| Total Weaned[2] | 13.2 | 13.1 | — | — |
| Piglet weights | | | | |
| Litter weight Pre fostering (kg) | 20.2 | 19.8 | 0.65 | 0.34 |
| Average birth weight (kg) | 1.38 | 1.36 | 0.04 | 0.29 |
| Litter weight post fostering (kg)[5] | 30.1 | 30.8 | 1.26 | 0.33 |
| Average weight post fostering (kg) | 2.26 | 2.30 | 0.09 | 0.35 |
| Litter weight at weaning (kg)[6] | 81.1 | 82.0 | 3.29 | 0.48 |
| Average weight at weaning (kg)[6] | 6.62 | 6.71 | 0.26 | 0.38 |
| ADG 0-5 (g/day)[6] | 154 | 157 | 16.31 | 0.62 |
| ADG 5-weaning (g/day)[7] | 245.9 | 245.3 | 10.75 | 0.88 |
| ADFI day 5-16 of age (grams/piglet/day) | 6.4 | 6.8 | 0.58 | 0.07 |
| ADFI day 16-23 of age (grams/piglet/day) | 20.3 | 20.6 | 2.49 | 0.88 |
| ADFI day 5-23 of age (grams/piglet/day) | 12.3 | 12.3 | 1.29 | 0.96 |
| Piglet mortality | | | | |
| Probability of piglets alive at day 4-5 (%)[8] | 92.8 | 92.5 | 0.9 | 0.73 |
| Probability of piglet mortality from cross fostering (day 4-5)-weaning (%)[8] | 1.9 | 2.0 | 0.6 | 0.86 |
| Probability of piglet Livability[7,8] | 89.5 | 89.8 | 1.8 | 0.81 |

[1] Bolifor CNF is a calciumnitrate source (5Ca(NO$_3$)$_2$•NH$_4$NO$_3$•10H$_2$O) containing 18.9% of Calcium and 63.1% of Nitrate.
[2] Numbers shown are means
[3] Numbers are corrected for lactation length and number of piglets weaned
[4] Sows were fed restricted. Feed intake reported is from farrowing till weaning.
[5] Is a calculated and not a measured value
[6] Are corrected for lactation length
[7] Piglet livability per sow is calculated by; 1-((number of stillborn + Number of piglets that died pre weaning)/total pigs after cross fostering))
[8] Induction of sows used as a covariable As generally shown in TABLE 1C, the addition of 0.1% calcium nitrate to the diet resulted in: (i) a numerically higher probability of born alive; (ii) a numerically lower probability of still born; (iii) a numerically higher probability of piglet livability; and (iv) a numerically higher litter weight at weaning.

Example 2

Example 2 determined the effect of calcium nitrate in the diet of a sow. 600 sows and all sows were fed two diets over the test period. The first diet (phase 1) was fed from approximately 5 days pre-farrowing until 5 days post-farrowing. The second diet (phase 2) was fed from day 5 post-farrowing until weaning. For the first 138 days both phase 1 and 2 diets did not contain any test product (i.e. negative control). For the subsequent 90 days, all sows were fed phase 1 diets that contained 1.0 kg/metric ton BOLIFOR CNF inorganic feed material of calcium nitrate feed grade (calcium nitrate, containing 63.1% of nitrate) commercially available from Yara Phosphates Oy of Helsingborg, Sweden (i.e. positive control). For the final 34 days both phase 1 and 2 diets did not contain any test product (i.e. negative control).

The following measurements were recorded as shown in TABLE 2A: (i) gestation length; (ii) sow reproductive performance was recorded right after farrowing (number of piglets born total, alive, stillborn); (iii) piglet; (iv) total piglets weaned; (v) weaning weights; and (vi) piglets per sow per year; and (v).

TABLE 2A

|  | No calcium nitrate 1 Jan. 2014 till 18 May 2014 | 0.1% Calcium nitrate 19 May 2014 till 16 Aug. 2014 | No calcium nitrate 17 Aug. 2014 till 20 Sep. 2014 |
|---|---|---|---|
| # Days | 138 | 90 | 34 |
| Pregnancy rate (%) | 92.6 | 94.5 | 98.1 |
| Gestation days | 118.2 | 118.2 | 117.7 |
| # Farrowings | 539 | 382 | 156 |
| Weaning age | 28.0 | 27.2 | 26.9 |
| Total Born | 18.0 | 17.3 | 18.2 |
| Born Alive | 16.0 | 15.8 | 16.3 |
| Still Born | 2.0 | 1.5 | 2.0 |
| Mortality (%) | 13.0 | 10.5 | 8.8 |
| Piglets Weaned | 13.9 | 14.3 | 14.0 |
| Weaning weight (kg) | 6.7 | 6.7 |  |
| Piglets/sow/year | 31.9 | 34.1 | 33.2 |
| Piglet Livability (%) | 77.2 | 82.7 | 81.9 |

As generally shown in TABLE 2A, feeding calcium nitrate resulted in: (i) a decrease in the number of stillborn; (ii) an increase in piglets weaned; and (iii) an increase in piglet livability.

Example 3

Example 3 is directed to the effect of calcium nitrate in lactation feed on reproduction performance of sows, number of stillborn piglets, placental blood flow and viability of piglets; demonstrating the lower probability on stillbirth of piglets and a higher probability of live born piglets.

Material and Methods

A field trial was conducted on a commercial farm in Denmark with 650 highly productive Danbred sows (Landrace x Yorkshire) inseminated with a pure line Duroc boar, between Nov. 17, 2014 and Jan. 16, 2015. A total of 139 sows (total number before analyzes) were included in the trial, divided over 3 subsequent sow groups farrowing over a time span of 6 weeks. For all analyzes SAS software (version 9.3, SAS Institute Inc., Cary, N.C.) was used. Sows received a dry meal transition feed (from gestation to lactation), fed from day 111 of gestation till day 5 of lactation, and were allocated to one of the two treatment groups based on parity. Sows in the control group received the transition feed without an addition of calcium nitrate ($5Ca(NO_3)_2 \cdot NH_4NO_3 \cdot 10H_2O$, Bolifor CNF® with 63.1% nitrate, Yara Animal Nutrition, Oslo, Norway) of 0.1% inclusion in final feed. The total amount of calcium was equal between both experimental treatments. Number born alive (NBA), stillborn and mummies, litter birth weight, as well as back fat of the sows before farrowing (day 110 of gestation) and at weaning (day 24 of lactation) were measured. Litter weights at 24 hours and 3 days after birth were measured as well. On day 3 after birth blood samples were taken from 6 piglets (2 biggest, 2 medium and 2 smallest) from 65 litters of their tails when they were cut and analyzed on immunoglobulin G (IgG) concentration. Placentas of the sows were collected after the farrowing process was finished, stored in freezers and afterwards scored on redness for an indication of the vascularization of these placentas.

Results

Absolute number of stillborn piglets was significantly lower in litters of sows receiving the 0.1% Bolifor CNF® compared to the control sows (1.32 vs. 1.79 respectively, $p<0.05$) and lower for parity 1 & 2 sows ($p<0.05$) compared to the control sows. An interaction between diet and parity is seen ($p=0.077$) for NBD. A trend can be seen for higher parities (>4), where addition of Bolifor CNF® shows a higher reduction of NBD for the highest parity group compared to the same parity group in the control group (2.51 vs. 1.21 for control and treatment group respectively). NBA was significantly higher in litters of sows receiving the 0.1% Bolifor CNF® compared to the control sows (16.84 vs. 16.34 respectively, $p<0.05$) and higher for parity 1 & 2 sows (17.14 vs. 16.36 and 16.27 for parity 1 & 2, parity 3 & 4 and parity>4 respectively. Birth weight ($p=0.291$), back fat loss ($p=0.748$) and TNB ($p=0.139$) did not differ between both diets. Weights and growth were higher in litters of sows receiving the 0.1% Bolifor CNF® compared to the control sows, however, litter start—($p=0.543$), litter 24 hour—($p=0.489$), and litter 3 days weight ($p=0.404$) did not differ between diets as did average piglet start—($p=0.803$), 24 hour—($p=0.549$) and 3 days weight ($p=0.478$). The same applies to growth where no differences were found between litters of sows receiving the 0.1% Bolifor CNF® compared to the control sows for litter growth from start to 24 hour weight ($p=0.542$), 24 hour to 3 days weight ($p=0.342$) and start to 3 days weight ($p=0.309$) as for average piglet growth from start to 24 hour weight ($p=0.675$), 24 hour to 3 days weight ($p=0.859$) and start to 3 days weight ($p=0.683$). No differences were found for calculated colostrum intake (CI) between diets ($p=0.409$) and parities ($p=0.335$). Mortality did not differ between sows receiving the 0.1% Bolifor CNF® and the control group ($p=0.630$) and no differences for mortality were found for parity ($p=0.212$). Standard deviation ($p=0.897$) and coefficient of variation within litters ($p=0.632$) of piglet serum IgG concentration did not differ between diets and parity ($p=0.919$ and $p=0.679$ respectively).

Supplementation of dietary nitrate decreased NBD and increased NBA. No differences were found on litter weights, growth, CI and IgG concentration. Earlier feeding or for a longer period may influence placental vascularity and therefore fetal development and piglet viability.

TABLE 3a

LS Means ± SEM and p-values of diet for different traits

|  | Control | Control + 0.1% Bolifor CNF ® | P-value |
|---|---|---|---|
| Number of sows | 65 | 58 |  |
| BF* Farrowing | 15.05 ± 0.74 | 15.44 ± 0.73 |  |
| BF Weaning | 12.44 ± 0.25 | 12.34 ± 0.25 |  |
| Lactation Days | 22.88 ± 1.08 | 23.19 ± 1.08 |  |
| Average parity | 3.37 ± 1.49 | 3.45 ± 1.45 |  |
| Gestation days | 117.40 ± 0.154 | 117.81 ± 0.152 | 0.062 |
| TNB* | 18.87 ± 0.464 | 17.90 ± 0.460 | 0.139 |
| NBA* | 16.34 ± 0.172 | 16.84 ± 0.170 | 0.039 |
| NBD*[1] | 1.79 ± 0.006 | 1.32 ± 0.006 | 0.043 |
| Birth weight (kg) | 21.15 ± 0.617 | 21.70 ± 0.614 | 0.291 |
| BF Loss (mm) | 2.71 ± 0.253 | 2.80 ± 0.241 | 0.748 |

*BF, Back Fat; TNB, Total Number Born; NBA, Number Born Alive; NBD, Number Born Death.
[1]Log transformed parameter, estimates are transformed back to absolute values.

TABLE 3b

LS Means ± SEM and p-values of diet for different traits

|  | Control | Control + 0.1% Bolifor CNF ® | P-value |
|---|---|---|---|
| Number of sows | 60 | 60 | |
| Number of piglets[1] | | | |
| Start | 13.10 | 12.65 | |
| 24 hour | 13.10 | 12.65 | |
| 3 days | 13.10 | 12.65 | |
| Litter weight (kg) | | | |
| Start | 17.05 ± 0.579 | 16.70 ± 0.572 | 0.543 |
| 24 hour | 18.04 ± 0.155 | 18.14 ± 0.153 | 0.489 |
| 3 days | 19.78 ± 0.228 | 19.93 ± 0.226 | 0.404 |
| Piglet weight (kg) | | | |
| Start | 1.31 ± 0.046 | 1.32 ± 0.046 | 0.803 |
| 24 hour | 1.40 ± 0.012 | 1.41 ± 0.012 | 0.549 |
| 3 days | 1.54 ± 0.018 | 1.55 ± 0.018 | 0.478 |
| Litter growth (kg/day) | | | |
| Start to 24 hour | 1.12 ± 0.163 | 1.21 ± 0.161 | 0.542 |
| 24 hour to 3 days | 1.69 ± 0.141 | 1.80 ± 0.140 | 0.342 |
| Start to 3 days | 2.83 ± 0.236 | 3.03 ± 0.234 | 0.309 |
| Piglet growth (kg/day) | | | |
| Start to 24 hour | 0.087 ± 0.013 | 0.093 ± 0.013 | 0.600 |
| 24 hour to 3 days | 0.132 ± 0.011 | 0.140 ± 0.011 | 0.373 |
| Start 3 days | 0.220 ± 0.018 | 0.235 ± 0.018 | 0.353 |
| Colostrum (g) | | | |
| CI* | 2688.30 ± 271.59 | 2858.60 ± 269.68 | 0.409 |
| CI per piglet | 207.60 ± 21.44 | 222.02 ± 21.29 | 0.377 |
| Mortality[2] | 1.72 ± 0.013 | 1.87 ± 0.012 | 0.630 |

*CI, Colostrum Intake.
[1]Means, numbers and weights are corrected for mortality and cross fostering.
[2]Log transformed parameter, estimates are transformed back to absolute values.

TABLE 3c

LS Means ± SEM and p-values of diet for immunoglobulin G (IgG) concentrations in piglet serum (mg IgG/ml)

|  | Control | Control + 0.1% Bolifor CNF ® | P-value |
|---|---|---|---|
| Number of sows | 60 | 60 | |
| IgG Average | 85.57 ± 19.53 | 80.29 ± 19.66 | 0.564 |
| IgG SD* | 28.90 ± 4.13 | 28.37 ± 4.26 | 0.897 |
| IgG CV* | 0.39 ± 0.13 | 0.42 ± 0.13 | 0.632 |

*SD, Standard deviation; CV, Coefficient of variation.

Example 4

Example 4 is directed to the effect of nitrate in the diet of a sow.

Materials and Methods

A trial was conducted at the Sterksel Research farm in the Netherlands (part of Wageningen University Research). A total of 207 sows were used in the trial allocated based on parity over 6 treatments (n=34). The sows entered the farrowing room day 107 of gestation and received from that moment onward one of the 6 treatments: being a standard lactation diet containing respectively 0.0% (negative control), 0.03%, 0.06%, 0.09%, 0.12% and 0.15% nitrate (mixing in the feed as calcium nitrate containing 63.1% nitrate) until 5 days after farrowing. Calcium levels were the same in all diets.

Until farrowing, sows received a fixed amount of feed (3.25 kg from day 107-113 and 2.7 kg/sow/day from day 113 till farrowing). During lactation the sows were fed the diets according to a step-up feeding schedule applied (increasing with 0.5 kg/sow/day) the same over the 6 treatments aiming at a peak intake of 7.5 kg/sow/day. Piglets were weaned from the sow at 27 days of age. Performance of sows (e.g. weight, backfat, piglets born alive, stillborn piglets, mortality of piglets) and piglets (e.g. weight at birth, after 48 hours and weaning) was measured on all sows and litters. A subset of sows (19-20 per treatment) was examined more in detail to get insight in the possible mode of action of nitrate. On this subset, blood samples were collected within 4 minutes after birth from 2 piglets out of every 4 piglets born. Blood gasses of umbilical cord blood were analyzed using the i-STAT handheld (Abbott). Vitality of piglets was scored within 30 seconds after birth according to Baxter et al. (2008) with 1 being the lowest and 4 being the highest score for vitality.

Results:

TABLE 4(a)

Sow body condition performance

| Variable | Level of Nitrate (%) | | | | | | P value |
| | 0 Treat1 | 0.03 Treat2 | 0.06 Treat3 | 0.09 Treat4 | 0.12 Treat5 | 0.15 Treat6 | Linear effect |
|---|---|---|---|---|---|---|---|
| Nr of replicates | 35 | 32 | 35 | 36 | 34 | 35 | — |
| Parity | 3.8 | 4.0 | 4.2 | 3.9 | 3.9 | 4.1 | — |
| Days on feed before farrowing | 7.7 | 7.4 | 7.2 | 7.3 | 7.9 | 7.5 | — |
| Backfat at day 107 of gestation (mm) | 15.8 | 15.1 | 16.1 | 16.3 | 15.7 | 17.5 | — |
| body weight after farrowing (kg) | 241.3 | 241.6 | 240.7 | 240.8 | 240.0 | 240.0 | 0.0670 |
| Suckling days | 26.5 | 26.8 | 26.9 | 26.9 | 26.3 | 26.5 | |
| Body weight at weaning (kg) | 232.0 | 228.5 | 228.1 | 226.6 | 224.8 | 227.5 | 0.0636 |

TABLE 4(a)-continued

Sow body condition performance

| Variable | Level of Nitrate (%) | | | | | | P value |
|---|---|---|---|---|---|---|---|
| | 0 Treat1 | 0.03 Treat2 | 0.06 Treat3 | 0.09 Treat4 | 0.12 Treat5 | 0.15 Treat6 | Linear effect |
| Backfat at weaning (mm) | 12.8 | 12.8 | 12.6 | 12.2 | 12.7 | 12.5 | 0.2952 |
| Body weight change during lactation | −10.0 | −13.4 | −12.8 | −15.0 | −15.4 | −13.3 | 0.1874 |
| % weight change farrow - wean | −3.5 | −5.4 | −5.0 | −5.9 | −6.3 | −4.8 | 0.2472 |
| Backfat change during lactation | −2.8 | −2.8 | −3.0 | −3.4 | −2.9 | −3.1 | 0.2952 |
| % backfat change | −17.7 | −17.0 | −19.4 | −21.6 | −18.2 | −19.3 | 0.3351 |

No clear statistical differences were found in these parameters. While there was a significant linear effect of nitrate on body weight at farrowing the low net change (1.8 kg difference across the nitrate range) is considered biologically insignificant. The trend in body weight at weaning could possibly be explained by higher total litter gain (see table 3) which would be associated with more milk production.

TABLE 4b sow reproductive performance

| Variable | Level of Nitrate (%) | | | | | | P value |
|---|---|---|---|---|---|---|---|
| | 0 Treat1 | 0.03 Treat2 | 0.06 Treat3 | 0.09 Treat4 | 0.12 Treat5 | 0.15 Treat6 | Linear effect |
| Total born | 16.3 | 16.8 | 16.8 | 16.1 | 17.1 | 16.6 | — |
| Total born alive | 15.1 | 15.2 | 15.7 | 14.9 | 15.8 | 15.3 | — |
| Total still born | 1.2 | 1.6 | 1.1 | 1.2 | 1.3 | 1.3 | — |
| Total born mummified | 0.3 | 0.6 | 0.7 | 0.5 | 0.5 | 0.3 | — |
| Total nr. of piglets after cross fostering | 14.7 | 15.0 | 14.8 | 14.4 | 14.7 | 14.8 | — |
| Total weaned | 12.3 | 12.3 | 12.4 | 12.7 | 13.0 | 12.6 | — |
| Average mortality % | 17.0 | 16.5 | 16.2 | 12.7 | 14.0 | 14.8 | — |
| Average livability % | 77.2 | 76.1 | 78.3 | 81.3 | 80.0 | 79.0 | — |
| Probability born alive | 0.96 | 0.95 | 0.97 | 0.96 | 0.96 | 0.96 | 0.8310 |
| Probability weaned | 0.91 | 0.91 | 0.91 | 0.94 | 0.93 | 0.92 | 0.0642 |
| Probability mortality | 0.10 | 0.10 | 0.10 | 0.07 | 0.08 | 0.09 | 0.1169 |
| Probability livability | 0.86 | 0.85 | 0.86 | 0.89 | 0.88 | 0.87 | 0.1322 |

Because of the non-normal distribution these parameters were statistically analyzed using probabilities.

Higher nitrate levels tended to lower mortality and increase livability, resulting in more weaned piglets per litter. Livability is defined as piglets weaned from total born corrected for cross fostering. Probability of weaned piglets tended ($P<0.10$) is improved with increasing nitrate inclusion.

TABLE 4c

Piglet technical performance

| Variable | Level of Nitrate (%) | | | | | | P value |
|---|---|---|---|---|---|---|---|
| | 0 Treat1 | 0.03 Treat2 | 0.06 Treat3 | 0.09 Treat4 | 0.12 Treat5 | 0.15 Treat6 | Linear effect |
| Aver. birth weight born alive pigs (grams) | 1262 | 1308 | 1320 | 1329 | 1326 | 1355 | 0.0228 |
| total birth weight litter life born piglets (kg) | 19.6 | 19.5 | 20.3 | 20.2 | 20.8 | 21.0 | 0.0341 |

TABLE 4c-continued

| | Piglet technical performance | | | | | | |
|---|---|---|---|---|---|---|---|
| | Level of Nitrate (%) | | | | | | P value |
| Variable | 0 Treat1 | 0.03 Treat2 | 0.06 Treat3 | 0.09 Treat4 | 0.12 Treat5 | 0.15 Treat6 | Linear effect |
| Average piglet weight after 48 hours (kg) | 1.582 | 1.611 | 1.598 | 1.621 | 1.640 | 1.692 | 0.0126 |
| Probability of a higher Vitality score | 0.75 | 0.70 | 0.74 | 0.80 | 0.78 | 0.79 | 0.0042 |
| Average weight at weaning (kg) | 7.431 | 7.439 | 7.321 | 7.472 | 7.550 | 7.608 | 0.1971 |
| total litter weight weaning (kg) | 92.2 | 91.8 | 91.8 | 96.9 | 98.6 | 96.8 | 0.0203 |

Increasing nitrate levels resulted in higher average piglet birth weight, total liter birth weight and average piglet weight at 48 h (P<0.05). Vitality score of the piglets is significantly (P<0.05) improved on increasing nitrate addition in the feed. Total litter weight at weaning is also significantly (P<0.05) improved. Increased weight at weaning suggests higher milk production TABLE 4d

| | blood parameters umbilical cord | | | | | | |
|---|---|---|---|---|---|---|---|
| | Treat1 | Treat2 | Treat3 | Treat4 | Treat5 | Treat6 | |
| | Level of Nitrate (%) | | | | | | Linear |
| Variable | 0 | 0.03 | 0.06 | 0.09 | 0.12 | 0.15 | effect |
| Nr of replicates | 20 | 19 | 20 | 20 | 19 | 19 | — |
| Parity | 4.1 | 4.1 | 4.0 | 4.0 | 3.8 | 4.1 | — |
| Days on feed before farrowing | 7.3 | 7.8 | 7.3 | 6.9 | 7.9 | 7.5 | — |
| Blood values umbilical cord piglets | | | | | | | |
| pH | 7.5 | 7.5 | 7.5 | 7.5 | 7.5 | 7.5 | 0.8473 |
| pCO2 (mmHg) - Measured value | 33.3 | 34.1 | 34.5 | 34.9 | 34.5 | 34.8 | 0.4116 |
| pO2 (mmHg) - Measured value | 31.1 | 33.8 | 35.4 | 34.5 | 35.6 | 35.3 | 0.0305 |

From these parameters, pO2 values were linearly improved by increasing nitrate addition. This higher amount of oxygen in the blood of piglets direct after birth is indicating less asphyxia during the birth process which could explain better vitality score shown in table 3 and a better vitality score could be the explanation that piglets grow faster during the rest of the suckling period because they suckle more vigorously.

The inclusion of nitrate in lactation feed for sows improves piglet's livability and enhances their body weight development. The hypotheses that nitrate in feed (via nitrite pathway) can lead to better oxygen supply is confirmed by the blood pO2 as measured in the umbilical cord of the piglets. This can explain the better vitality score of the fresh born piglets. Statistics show several linear effects suggesting that the higher the dose the better. Looking at the figures numerically, some characteristics reach their optimum already at 0.09% nitrate inclusion. An optimal dose is not clear cut but seems to be somewhere between 0.09 and 0.15% added nitrate.

We claim:

1. A premix comprising:
one or more nitrate compounds in the amount of greater than about 50% by weight of the premix; and
vitamins and trace minerals;
wherein:
the premix is formulated for use in at least one of a gestation or lactation phase of an animal in an amount of less than about five percent by weight (5.0 wt %) inclusion per metric ton of a complete animal feed;
the complete animal feed is a gestation feed or a lactation feed; and
the one or more nitrate compounds increase vasodilation of the placenta and the mammary glands of the animal.

2. The premix of claim 1, wherein the one or more nitrate compounds comprise at least one chosen from calcium nitrate and its related salts.

3. The premix of claim 2, wherein the calcium nitrate and its related salts comprise at least about 15% calcium and at least about 10% nitrogen.

4. The premix of claim 2, wherein the calcium nitrate and its related salts are prilled.

5. The premix of claim 1, wherein the one or more nitrate compounds comprise ten hydrated calcium ammonium nitrate $5Ca(NO_3)_2 \cdot NH_4NO_3 \cdot 10H_2O$.

6. The premix of claim 1, wherein the at least one nitrate compound comprises at least one chosen from magnesium nitrate and its related salts.

7. The premix of claim 1, wherein the at least one nitrate compound comprises magnesium nitrate hexahydrate (Mg(NO$_3$)$_2$·6H$_2$O).

8. The premix of claim 1, wherein the premix is formulated for inclusion in a complete animal feed.

9. A complete animal feed comprising:
the premix of claim 1, wherein the premix is less than about five percent by weight (5.0 wt %) of the complete animal feed.

10. The complete animal feed of claim 9, wherein the complete animal feed is a gestation feed, wherein the complete animal feed is further comprising:
14.0 wt % Protein, 4.5 wt % Fat, 12.0 wt % Moisture, 5.0 wt % Fiber, 0.8 wt % Calcium, 0.5 wt % Phosphorus, and 0.5 wt % Lysine; or
15.0 wt % Protein, 6.0 wt % Fat, 12.0 wt % Moisture, 7.0 wt % Fiber, 0.9 wt % Calcium, 0.7 wt % Phosphorus, and 0.6 wt % Lysine.

11. The complete animal feed of claim 9, wherein the complete animal feed is a lactation feed, wherein the complete animal feed is further comprising:
18.0 wt % Protein, 6.0 wt % Fat, 12.0 wt % Moisture, 3.2 wt % Fiber, 0.9 wt % Calcium, 0.6 wt % Phosphorus, and 0.9 wt % Lysine; or
24.0 wt % Protein, 6.0 wt % Fat, 12.0 wt % Moisture, 5.0 wt % Fiber, 1.0 wt % Calcium, 0.7 wt % Phosphorus, and 0.9 wt % Lysine.

12. The complete animal feed of claim 10, wherein the complete animal feed is a gestation feed, wherein the complete animal feed is further comprising:
14.0 wt % Protein, 4.5 wt % Fat, 12.0 wt % Moisture, 5.0 wt % Fiber, 0.8 wt % Calcium, 0.5 wt % Phosphorus, and 0.5 wt % Lysine; or
15.0 wt % Protein, 6.0 wt % Fat, 12.0 wt % Moisture, 7.0 wt % Fiber, 0.9 wt % Calcium, 0.7 wt % Phosphorus, and 0.6 wt % Lysine.

13. The complete animal feed of claim 10, wherein the complete animal feed is a lactation feed, wherein the complete animal feed is further comprising:
18.0 wt % Protein, 6.0 wt % Fat, 12.0 wt % Moisture, 3.2 wt % Fiber, 0.9 wt % Calcium, 0.6 wt % Phosphorus, and 0.9 wt % Lysine; or
24.0 wt % Protein, 6.0 wt % Fat, 12.0 wt % Moisture, 5.0 wt % Fiber, 1.0 wt % Calcium, 0.7 wt % Phosphorus, and 0.9 wt % Lysine.

* * * * *